(12) United States Patent
Thorlakson et al.

(10) Patent No.: US 12,263,124 B2
(45) Date of Patent: Apr. 1, 2025

(54) OPHTHALMOLOGICAL DEVICE FOR INTRA-CAPSULAR FRAGMENTATION OF A LENS NUCLEUS

(71) Applicant: Ziemer Ophthalmic Systems AG, Port (CH)

(72) Inventors: Richard Thorlakson, Phoenix, AZ (US); Thomas Asshauer, Aarau (CH); Christian Rathjen, Bremen (DE)

(73) Assignee: Ziemer Ophthalmic Systems AG, Port (CH)

( * ) Notice: Subject to any disclaimer, the term of this patent is extended or adjusted under 35 U.S.C. 154(b) by 594 days.

(21) Appl. No.: 17/089,863

(22) Filed: Nov. 5, 2020

(65) Prior Publication Data

US 2021/0128360 A1 May 6, 2021

(30) Foreign Application Priority Data

Nov. 5, 2019 (EP) .................... 19207265

(51) Int. Cl.
*A61F 9/008* (2006.01)
(52) U.S. Cl.
CPC .............. *A61F 9/00836* (2013.01); *A61F 2009/00889* (2013.01)
(58) Field of Classification Search
CPC ........ A61F 9/00836; A61F 2009/00889; A61F 2009/00887; A61F 2009/00897; A61F 9/00825; A61F 9/00736
See application file for complete search history.

(56) References Cited

U.S. PATENT DOCUMENTS

| | | | |
|---|---|---|---|
| 2005/0165387 A1 | 7/2005 | Lubatschowski et al. | |
| 2014/0135752 A1 | 5/2014 | Duma et al. | |
| 2014/0330260 A1 | 11/2014 | Bergt et al. | |
| 2018/0263758 A1* | 9/2018 | Culbertson | ........... A61F 2/1637 |
| 2019/0083305 A1 | 3/2019 | Palanker et al. | |

FOREIGN PATENT DOCUMENTS

DE 102017216136 A1 3/2019

OTHER PUBLICATIONS

Mar. 13, 2020—(EP) Search Report—App 19207265.0.

* cited by examiner

*Primary Examiner* — Tammie K Marlen
*Assistant Examiner* — Ranjani Mari Sundaresan
(74) *Attorney, Agent, or Firm* — Banner & Witcoff, Ltd.

(57) ABSTRACT

An ophthalmological device for intracapsular fragmentation of a lens nucleus of an eye comprises a laser source, a focusing optical module, and a scanner system for moving a focus to target locations in the lens nucleus. For the fragmentation of the lens nucleus, an electronic circuit controls the scanner system to move the focus to intracapsular target locations on cutting planes which extend from a posterior surface to an anterior surface of the lens nucleus. The cutting planes form a maximum of two intracapsular intersecting lines on any of the cutting planes. Two of the cutting planes are arranged at a mutual distance larger than a diameter of a phaco handpiece tip and divide the lens nucleus into three fragments.

21 Claims, 6 Drawing Sheets

OPHTHALMOLOGICAL DEVICE FOR INTRA-CAPSULAR FRAGMENTATION OF A LENS NUCLEUS

CROSS-REFERENCE TO RELATED APPLICATION

The present application claims priority to and the benefit of European Patent Application 19207265.0 filed Nov. 5, 2019, which is incorporated by reference in its entirety herein.

FIELD OF TECHNOLOGY

The present disclosure relates to an ophthalmological device for intracapsular fragmentation of a lens nucleus. Specifically, the present disclosure relates to an ophthalmological device for intracapsular fragmentation of a lens nucleus of an eye, preparatory to emulsification and removal of the lens nucleus from the eye using a phaco handpiece tip.

BACKGROUND

A cataract is a clouding of the lens in the eye which leads to a decrease in vision. In cataract surgery, the clouded lens is removed and replaced with an artificial lens. The removal of the lens on human eyes is typically performed through emulsification of the lens. Using a phaco system, emulsification of the lens is achieved by means of an ultrasonic tip of a so-called "phaco handpiece". During a so called "phaco emulsification", the lens tissue is emulsified by the ultrasound emitted by the tip of the phaco handpiece while the emulsified tissue material is simultaneously aspirated by a pump of the phaco system through an opening in the phaco handpiece. Optionally, the phaco emulsification procedure is preceded by pre-fragmentation of the lens with a femtosecond laser device. The pre-fragmentation facilitates the subsequent removal process in that it reduces the amount of ultrasound energy and manual manipulations by the surgeon, which could cause damage to the corneal endothelial cells and the rim of the "capsulotomy", the opening in the anterior lens capsule created prior to lens removal for intracapsular access. Correspondingly, the safest place to emulsify lens fragments is in the middle of the anterior chamber of the eye, away from both the endothelium and the lens capsule.

Preparatory to emulsification and removal of the lens nucleus from the eye using a phaco handpiece tip, intracapsular fragmentation of the lens nucleus using a laser system is typically performed by a standard lens fragmentation pattern of four to eight sectors in the shape of "pizza" or "pie" slices. This typical fragmentation pattern is directly derived from manual cataract surgery methods, which use for example a so-called "chopping" technique employing the phaco tip and an additional spatula-like tool held by the other hand of the surgeon to split the lens into segments by applying solely mechanical force. To apply this force manually in a very precisely controlled way takes a lot of experience and a long learning curve, given that substantial force is needed to split hard cataract lens nuclei, but on the other hand excess force can easily damage the delicate structures around the lens such as the capsule rim or the zonula fibers connecting the lens with the surrounding eye. A further disadvantage of these "pie"-fragmentation patterns is that the first pie-slice-shaped wedge cannot be moved and pulled out easily with the phaco handpiece tip, because it is mechanically held in position by other slices or sectors of the lens nucleus. This requires further delicate, time-consuming and hard to learn maneuvers with the phaco tip to gently emulsify and remove a first piece of the "pie" in situ. In alternative fragmentation patterns, as an overlay to the standard "pizza" or "pie" sliced pattern, additional cube or stick patterns are cut by the femtosecond laser to create smaller pieces in the center of the lens center which, in principle, could be removed individually with the phaco handpiece tip. However, the cutting of these additional smaller pieces of lens nucleus has the disadvantage that much more laser energy is emitted into the eye, with increased risks of side effects, and that more time is needed for the procedure. In addition, these smaller tissue pieces can easily come loose prematurely or simultaneously during the procedural manipulation by the surgeon, leaving some of them bouncing around in the anterior chamber in the liquid flow of the aspiration pump. As a result, there is a risk of damage to the endothelial cells caused through mechanical impact of loose lens pieces. Furthermore, these patterns cannot be extended all the way to the periphery of the lens because access to the peripheral regions is restricted for the laser by the limited diameter or opening of the pupil. The worst case result of fragmentation is considered the removal of the lens tissue from the center of the nucleus while leaving a rim of remaining tissue in the periphery and at the bottom (posterior surface) of the nucleus, often called a "rice bowl shape", which is very difficult to further separate into manageable pieces of tissue.

SUMMARY

This disclosure provides an ophthalmological device for intracapsular fragmentation of a lens nucleus, which ophthalmological device does not have at least some of the disadvantages of the prior art. In particular, the present disclosure provides an ophthalmological device which makes the procedure for intracapsular fragmentation and removal of a lens nucleus easier for surgeons while reducing the risk of potentially harmful side-effects and thus making the procedure safer for patients.

According to the present disclosure, advantages are achieved through the features of the independent claims. In addition, further advantages follow from the dependent claims and the description.

An ophthalmological device for intracapsular fragmentation of a lens nucleus of an eye, preparatory to emulsification and removal of the lens nucleus from the eye using a phaco handpiece tip, comprises a laser source configured to generate a pulsed laser beam; a focusing optical module configured to make the pulsed laser beam converge onto a focus in the lens nucleus; and a scanner system configured to move the focus to target locations in the lens nucleus.

It is pointed out that the term "intracapsular" is used herein to refer to tissue or locations inside the lens capsule. In other words, "intracapsular" refers to tissue and locations of the lens nucleus which is inside the lens capsule, it does not refer to tissue and locations of the lens capsule itself. Accordingly, an "intracapsular" tissue cut is a cut of the tissue of the lens nucleus, it is not a cut of tissue of the lens capsule.

According to the present disclosure, the ophthalmological device for intracapsular fragmentation of the lens nucleus further comprises an electronic circuit configured to control the scanner system to move the focus to intracapsular target locations on cutting planes which extend from a posterior surface of the lens nucleus to an anterior surface of the lens nucleus for generating intracapsular tissue cuts for the fragmentation of the lens nucleus, whereby the cutting planes form a maximum of two intracapsular intersecting lines on any of the cutting planes, a first cutting plane and a second cutting plane are arranged at a mutual distance larger than a diameter of the phaco handpiece tip, have an optical axis of the lens nucleus running therebetween without intracapsular intersection, and divide the lens nucleus into three fragments, and a third cutting plane forms intracapsular intersecting lines with the first cutting plane and the second cutting plane for subdividing each of the three fragments. The intracapsular tissue cuts formed on the three cutting planes make it possible to create a first (initial) void inside the lens nucleus by removing the top part of the fragment under the main corneal incision by simple so-called "grooving" movement of the phaco tip, which constitute some of the most elementary techniques taught to novice eye surgeons. Once created, this initial void provides manoeuvring space and access thereto for handling the other fragments. It is much easier and more efficient to separate some of the lens nucleus fragments along the laser-prefragmented cutting planes, and one by one emulsify and remove them with the phaco tip. Owing to the laser-prefragmentation and the presence of the initially created void, only very little force is required for the separation of the fragments, making this method safer and more efficient than the traditional approaches described above, even for relatively inexperienced eye surgeons.

In an illustrative example, the electronic circuit is configured to control the scanner system to move the focus to intracapsular target locations on the first cutting plane and the second cutting plane whereby the first cutting plane and the second cutting plane are running essentially parallel to the optical axis of the lens nucleus.

In an illustrative example, the electronic circuit is configured to control the scanner system to move the focus to intracapsular target locations on the first cutting plane and the second cutting plane whereby the first cutting plane and the second cutting plane are running essentially parallel to each other.

In an illustrative example, the electronic circuit is configured to control the scanner system to move the focus to intracapsular target locations on the first cutting plane and the second cutting plane whereby the first cutting plane and the second cutting plane are inclined to each other and form an intersecting line outside the lens nucleus.

In an illustrative example, the electronic circuit is configured to control the scanner system to move the focus to intracapsular target locations on the first cutting plane and the second cutting plane whereby the first cutting plane and the second cutting plane are inclined to each other, defining an inclination angle in a reference plane normal to the optical axis of the lens nucleus.

In an illustrative example, the electronic circuit is configured to control the scanner system to move the focus to intracapsular target locations on the first cutting plane and the second cutting plane whereby the first cutting plane and the second cutting plane are inclined to each other, defining an inclination angle in a reference plane normal to a symmetry plane and running through the optical axis of the lens nucleus.

In an illustrative example, the electronic circuit is configured to control the scanner system to move the focus to intracapsular target locations on the first cutting plane and the second cutting plane whereby the first cutting plane and the second cutting plane have a symmetry plane running through the optical axis of the lens nucleus.

In an illustrative example, the electronic circuit is configured to control the scanner system to move the focus to intracapsular target locations on the third cutting plane whereby the third cutting plane is essentially parallel to the optical axis of the lens nucleus, e.g. through the optical axis of the lens nucleus.

In an illustrative example, the electronic circuit is configured to control the scanner system to move the focus to intracapsular target locations along adjacent scanning lines running in the cutting planes for generating the intracapsular tissue cuts.

In an illustrative example, the laser source comprises a femtolaser configured to generate a pulsed laser beam with femtosecond laser pulses.

In an illustrative example, the focusing optical module comprises at least one movable lens configured to adjust a location of the focus along the optical axis of the lens nucleus.

In an illustrative example, the scanner system comprises a divergence modulator configured to modulate a divergence of the pulsed laser beam for adjusting a location of the focus along the optical axis of the lens nucleus.

In an illustrative example, the distance between the first cutting plane and the second cutting plane is greater than a third of a diameter of the lens nucleus.

In an illustrative example, the electronic circuit is configured to control the scanner system to move the focus to intracapsular target locations on the first cutting plane, and the third cutting plane, whereby the first cutting plane, the second cutting plane, and the third cutting plane form an essentially H-shaped intersection with a reference plane normal to the optical axis of the lens nucleus.

In addition to the ophthalmological device for intracapsular fragmentation of the lens nucleus, the present disclosure also relates to a computer program product comprising a non-transitory computer-readable medium having stored thereon computer program code for controlling a processor of an ophthalmological device which comprises a laser source configured to generate a pulsed laser beam, a focusing optical module configured to make the pulsed laser beam converge onto a focus in a lens nucleus of an eye, and a scanner system configured to move the focus to target locations in the lens nucleus, whereby the computer program code is configured to control the processor such that the processor: directs the scanner system to move the focus to intracapsular target locations on cutting planes which extend from a posterior surface of the lens nucleus to an anterior surface of the lens nucleus for generating intracapsular tissue cuts for the fragmentation of the lens nucleus, whereby the cutting planes form a maximum of two intracapsular intersecting lines on any of the cutting planes, a first cutting plane and a second cutting plane are arranged at a mutual distance larger than a diameter of the phaco handpiece tip, have an optical axis of the lens nucleus running therebetween without intracapsular intersection, and divide the lens nucleus into three fragments, and a third cutting plane forms intracapsular intersecting lines with the first cutting plane and the second cutting plane for subdividing each of the three fragments.

BRIEF DESCRIPTION OF THE DRAWINGS

The present disclosure will be explained in more detail, by way of example, with reference to the drawings in which.

DETAILED DESCRIPTION

Figure 1:
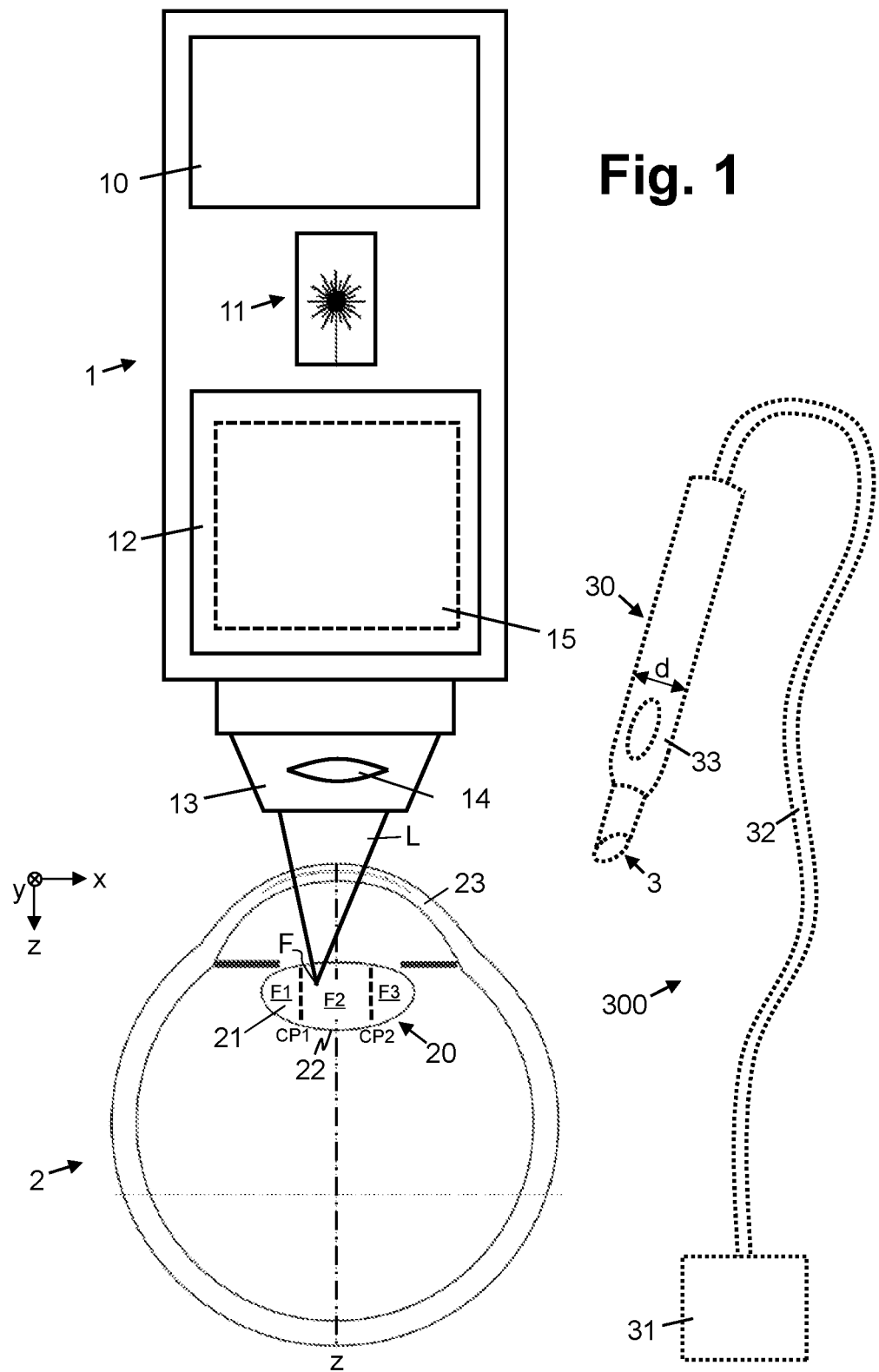
FIG. 1 shows a block diagram illustrating schematically an ophthalmological device for intracapsular fragmentation of a lens nucleus of an eye, preparatory to emulsification and removal of the lens nucleus from the eye using a phaco handpiece tip.

In FIG. 1, reference numeral 300 refers to a phaco emulsification system which comprises a phaco handpiece 30, also referred to as phaco probe, with an ultrasonic phaco handpiece tip 3 for emulsifying tissue of the lens nucleus 21 of a lens 20 of a human eye 2, and a vacuum pump 31 for aspiration of the emulsified lens tissue through a fluid conduit 32 for extracting and removing the lens nucleus 21 from the lens capsule 22. The diameter d of the phaco handpiece tip 3, including its sleeve 33 for interconnecting the fluid conduit, is typically in the range of 1 mm to 2 mm; the diameter of the actual phaco handpiece tip 3 (without its sleeve) is typically in the range of 0.5 mm to 1.2 mm; the diameter of the lens nucleus is typically in the range of 7 mm to 9 mm.

In FIG. 1, reference numeral 1 refers to an ophthalmological device for intracapsular fragmentation of the lens nucleus 21 of the lens 20 of the eye 2 before and in preparation of the procedure for emulsification of the lens nucleus 21 and removal and extraction of the lens nucleus 21 from the eye 2, using the phaco handpiece tip 3 of the phaco emulsification system 300.

The ophthalmological device 1 for intracapsular fragmentation comprises a laser source 11, a focusing optical module 13, a scanner system 12, and an electronic circuit 10 for controlling operation of the ophthalmological device 1 and its functional modules.

The laser source 11 is configured to generate a pulsed laser beam L, e.g. a femtolaser configured to generate a pulsed laser beam L with femtosecond laser pulses.

The focusing optical module 13 comprises one or more optical lenses and is configured to make the pulsed laser beam L converge onto a (punctiform) focus F in the lens nucleus 21. In an embodiment, the focusing optical module 13 comprises one or more movable lenses 14 configured to adjust the location of the focus F in the direction of projection of the focusing optical module 13, e.g. along the optical axis z of the lens nucleus 21.

The scanner system 12 is configured to move the focus F to target locations in the lens nucleus 21. The scanner system 12 comprises one or more movable optical deflectors, e.g. rotatable mirrors, configured to deflect the pulsed laser beam L to move the focus F to target locations in the lens nucleus 21. In an embodiment, the scanner system 12 comprises a divergence modulator 15 configured to modulate a divergence of the pulsed laser beam L for adjusting the location of the focus F in the direction of projection of the focusing optical module 13, e.g. along the optical axis z of the lens nucleus 21. The scanner system 12 is controlled by the electronic circuit 10, e.g. by way of control signals and/or commands via interconnecting control lines.

One skilled in the art will understand that for controlling the scanner system 12 to direct and move the focus F to target locations in the lens nucleus 21, the electronic circuit 10 uses stored operation and eye data (e.g. OCT data of the eye 2), defining the target locations in the lens nucleus 21 for the planned operation of intracapsular fragmentation with regards to the actual eye 2 to be treated. One skilled in the art will further understand that for performing the operation of intracapsular fragmentation, the eye 2 will be fixed to an applicator of the ophthalmological device 1, e.g. to the focusing optical module 13, and/or the ophthalmological device 1 comprises an eye tracking system configured to determine and provide to the electronic circuit 10 current eye position data, during the intracapsular fragmentation operation, such as to enable the electronic circuit 10 to control the scanner system 12 to direct and move the focus F to the planned target locations in the lens nucleus 21.

Figure 4:
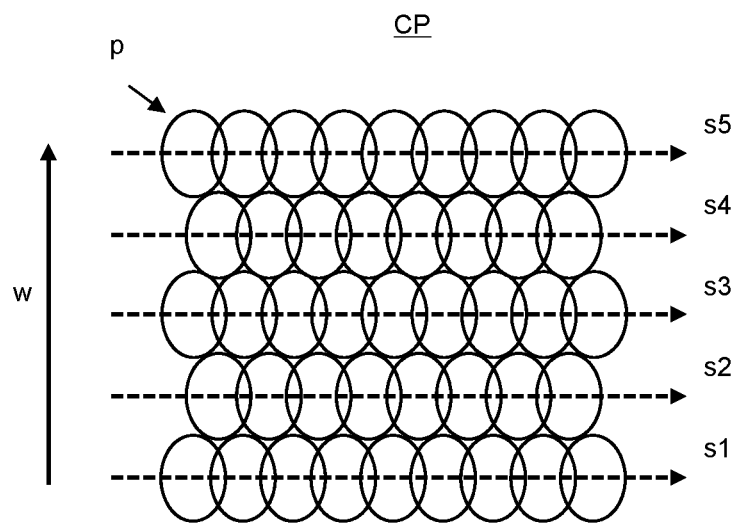
FIG. 4 shows a schematic example of adjacent scanning lines with partially overlapping laser pulses in a cutting plane for producing a tissue cut.

Depending on the embodiment, the electronic circuit 10 is implemented as a programmable processor, an application specific integrated circuit (ASIC), or another programmable logic unit. The processor is controlled by computer program code stored on a non-transitory computer-readable medium of a computer program product. The electronic circuit 10 or its computer program code, respectively, is configured to control the ophthalmological device 1 and its functional modules to execute various functions and steps as outlined below in more detail. Specifically, the electronic circuit 10 or its computer program code, respectively, is configured to control the scanner system 12. More specifically, the electronic circuit 10 or its computer program code, respectively, is configured to control the scanner system 12 to move the focus F to intracapsular target locations. For producing intracapsular tissue cuts, the electronic circuit 10 or its computer program code, respectively, is configured to control the scanner system 12 to move the focus F to intracapsular target locations along adjacent scanning lines s1, s2, s3, s4, s5, e.g. with partially overlapping spots of the laser pulses p, running in a defined cutting plane CP for generating the intracapsular tissue cut, whereby the scanning lines s1, s2, s3, s4, s5 are processed in a bottom-up working direction w (i.e. reverse to the direction of projection of the focusing optical module 13), as illustrated in FIG. 4.

Figure 2:
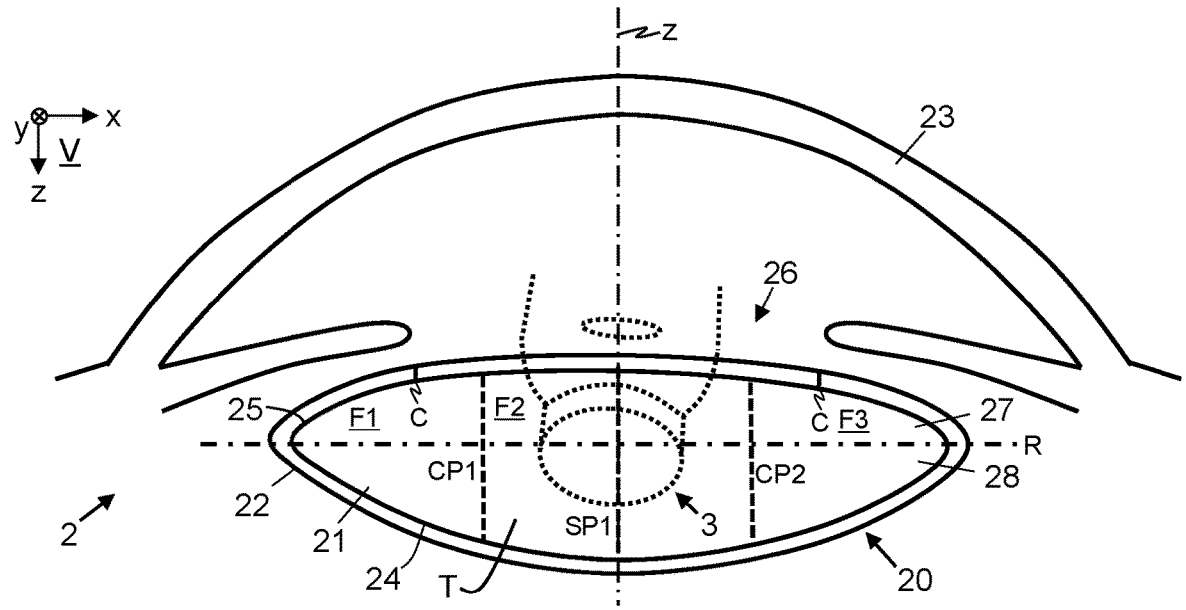
FIG. 2 shows a schematic cross section of a human eye with two intracapsular tissue cuts, which divide the lens nucleus into three fragments and run along cutting planes extending from the posterior surface of the lens nucleus to the anterior surface of the lens nucleus, essentially parallel to each other and to the optical axis of the lens nucleus.
Figure 3:
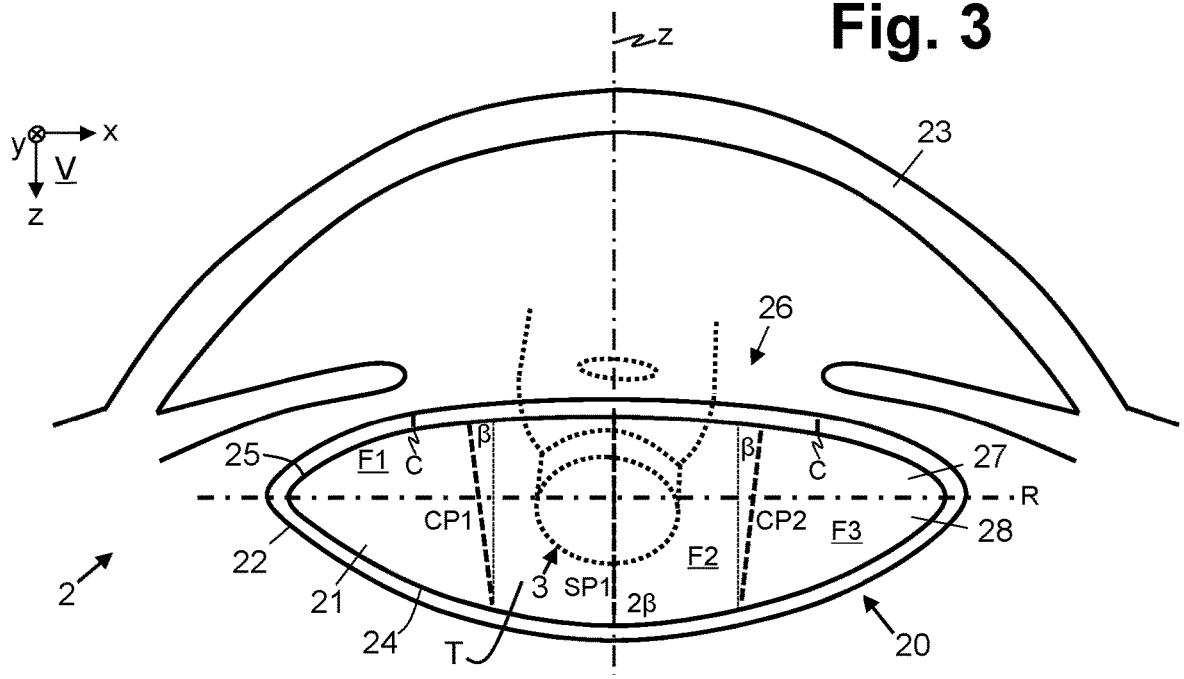
FIG. 3 shows a schematic cross section of a human eye with two intracapsular tissue cuts, which divide the lens nucleus into three fragments and run along cutting planes extending from the posterior surface of the lens nucleus to the anterior surface of the lens nucleus and are inclined to each other to form an intersecting line outside the lens nucleus.
Figure 6:
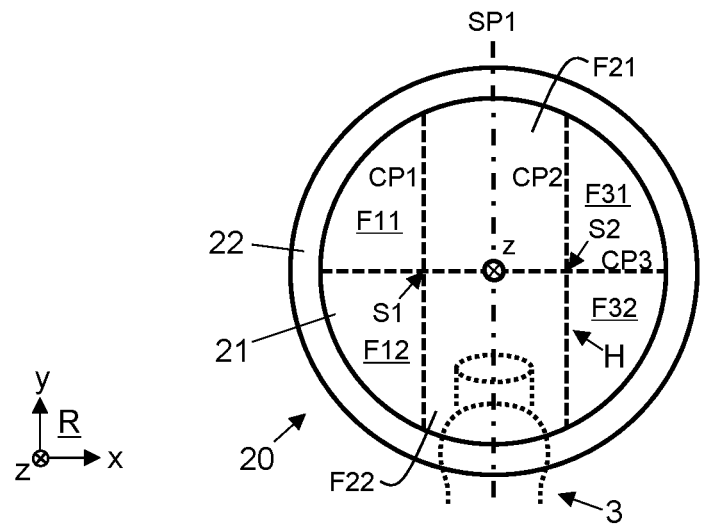
FIG. 6 shows a schematic top view of a lens of a human eye with two intracapsular tissue cuts, which divide the lens nucleus into three fragments and run along cutting planes, essentially parallel to each other and to the optical axis of the lens nucleus, whereby a third tissue cut runs along a cutting plane which runs essentially parallel to the optical axis of the lens nucleus and subdivides the three fragments.
Figure 7:
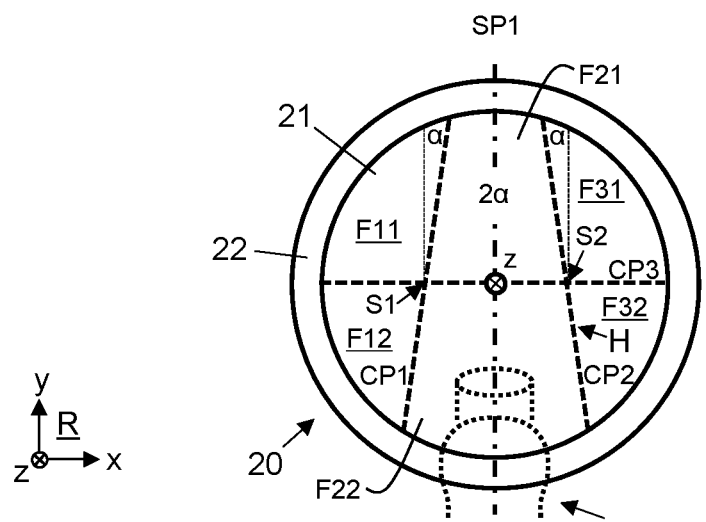
FIG. 7 shows a schematic top view of a lens of a human eye with two intracapsular tissue cuts, which divide the lens nucleus into three fragments and run along cutting planes, inclined to each other to form an intersecting line outside the lens, whereby a third tissue cut runs along a cutting plane which runs through the optical axis of the lens nucleus and subdivides the three fragments.

For producing an intracapsular fragmentation of the lens nucleus 21 with the advantageous fragmentation pattern according to the disclosure, the electronic circuit 10 or its computer program code, respectively, is configured to control the scanner system 12 to move the focus F to intracapsular target locations on three cutting planes CP1, CP2, CP3 which extend from a posterior surface 24 of the lens nucleus 21, averted away from the pupil 26 and cornea 23, to an anterior surface 25 of the lens nucleus 21, facing the pupil 26 and cornea 23, for generating the intracapsular tissue cuts for the fragmentation of the lens nucleus 21, whereby the first cutting plane CP1, the second cutting plane CP2, and the third cutting plane CP3 form an essentially H-shaped intersection H, as is illustrated in the top views of FIGS. 6 and 7, with an x/y-reference plane R which is normal to the optical axis z of the lens nucleus 21 and divides the lens 20 into a top lens part 27, facing the pupil 26 and cornea 23, and a bottom lens part 28, averted away from the pupil 26 and cornea 23, as is illustrated in the cross sections of FIGS. 2 and 3. As illustrated in FIGS. 6 and 7, the H-shaped intersection H of the first cutting plane CP1, the second cutting plane CP2, and the third cutting plane CP3 with the lens nucleus 21 defines and forms six nucleus fragments F11, F12, F21, F22, F31, F32 as will be described in more detail below. In the following paragraphs, the fragmentation of the lens nucleus 21 with such an H-shaped intersection H is also referred to as H-shaped fragmentation of the lens nucleus 21.

Figure 5:
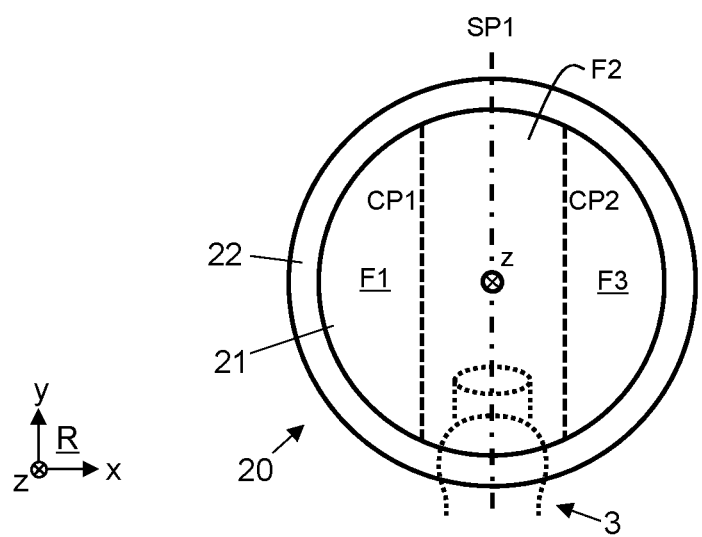
FIG. 5 shows a schematic top view of a lens of a human eye with two intracapsular tissue cuts, which divide the lens nucleus into three fragments and run along cutting planes extending from the posterior surface of the lens nucleus to the anterior surface of the lens nucleus, essentially parallel to each other and to the optical axis of the lens nucleus.

For generating the H-shaped fragmentation of the lens nucleus 21, the electronic circuit 10 or its computer program code, respectively, is configured to control the scanner system 12 to produce intracapsular tissue cuts by moving the focus F to intracapsular target locations on three cutting planes CP1, CP2, CP3 which are defined by the following attributes:

1) The three cutting planes CP1, CP2, CP3 and the respective intracapsular tissue cuts extend from the posterior surface 24 of the lens nucleus 21 to the anterior surface 25 of the lens nucleus 21;
2) The three cutting planes CP1, CP2, CP3 and the respective intracapsular tissue cuts are arranged such that they form a maximum of two intracapsular intersecting lines S1, S2 on any of the cutting planes CP1, CP2, CP3, i.e. inside the lens capsule 22, each of the three cutting planes CP1, CP2, CP3 and the respective intracapsular tissue cuts is intersected at most twice by the other two cutting planes CP1, CP2, CP3 or respective intracapsular tissue cuts, respectively;
3) Two of the three cutting planes CP1, CP2 and the respective intracapsular tissue cuts are arranged at a mutual distance slightly larger than a diameter of the phaco handpiece tip 3 with sleeve (typically in a range greater than 1 mm to 2 mm), whereby the optical axis z of the lens nucleus 21 runs between these two cutting planes CP1, CP2, without intracapsular intersection with the two cutting planes CP1, CP2, such that the intracapsular tissue cuts produced on the two cutting planes CP1, CP2 divide the lens nucleus 21 into three lens nucleus fragments F1, F2, F3, as illustrated in FIGS. 2, 3 and 5, basically dividing the lens nucleus 21 into three slices: an intermediary central slice, corresponding to lens nucleus fragment F2, which is in a favourable embodiment aligned with the corneal incision used for access by the phaco handpiece, and two neighbouring exterior slices, corresponding to lens nucleus fragments F1 and F3); and
4) The remaining third of the three cutting planes CP3 and the respective intracapsular tissue cut forms intracapsular intersecting lines S1, S2 with the two other cutting planes CP1, CP2 such as to subdivide each of the three fragments F1, F2, F3, i.e. inside the lens capsule 22, the third cutting plane CP3 and the respective intracapsular tissue cut intersects with both of the other two cutting planes CP1, CP2, or respective intracapsular tissue cuts, respectively, and divides the three nucleus fragments F1, F2, F3 into a total of six lens nucleus fragments F11, F12, F21, F22, F31, F32, as illustrated in FIGS. 5, 6, 7, 8, 9 and 10, basically dividing each of the three slices (fragments F1, F2, F3) into two slice parts (lens nucleus fragments F11, F12, F21, F22, F31, F32).

In the embodiments illustrated in FIGS. 2, 3, 5, 6, and 7, the electronic circuit 10 or its computer program code, respectively, is configured to control the scanner system 12 to produce intracapsular tissue cuts by moving the focus F to intracapsular target locations on three cutting planes CP1, CP2, CP3 whereby two of the three cutting planes CP1, CP2 have a mutual symmetry plane SP1 which runs through the optical axis z of the lens nucleus 21.

In the embodiments illustrated in FIGS. 2, 5, 6, and 7, the electronic circuit 10 or its computer program code, respectively, is configured to control the scanner system 12 to produce intracapsular tissue cuts by moving the focus F to intracapsular target locations on three cutting planes CP1, CP2, CP3 whereby two of the cutting planes CP1, CP2 are running essentially parallel to the optical axis z of the lens nucleus 21.

In the embodiments illustrated in FIGS. 2, 5, and 6, the electronic circuit 10 or its computer program code, respectively, is configured to control the scanner system 12 to produce intracapsular tissue cuts by moving the focus F to intracapsular target locations on three cutting planes CP1, CP2, CP3 whereby two of the cutting planes CP1, CP2 are running essentially parallel to each other.

In the embodiments illustrated in FIGS. 3 and 7, the electronic circuit 10 or its computer program code, respectively, is configured to control the scanner system 12 to produce intracapsular tissue cuts by moving the focus F to intracapsular target locations on three cutting planes CP1, CP2, CP3 whereby two of the cutting planes CP1, CP2 are inclined to each other at such an angle that they intersect outside the lens nucleus 21, i.e. they form an intersecting line outside the lens nucleus 21.

In the embodiment illustrated in FIG. 7, the two cutting planes CP1, CP2 are inclined to each other such that they define an inclination angle $2\alpha$ in an x/y-reference plane R normal to the optical axis z of the lens nucleus 21, e.g. an inclination angle $2\alpha$ in a range of 10° to 20°. In the embodiment of FIG. 7, the two cutting planes CP1, CP2 are each inclined in such a way that their respective intersecting lines with the x/y-reference plane R have an inclination angle α to the intersecting line of the x/y-reference plane R with the mutual symmetry plane SP1 of the two cutting planes CP1, CP2, e.g. an inclination angle α in a range of 5° to 10°.

In the embodiment illustrated in FIG. 3, the two cutting planes CP1, CP2 are inclined to each other such that they define an inclination angle 2β in an x/z-reference plane V normal to a mutual symmetry plane SP1 and running through the optical axis z of the lens nucleus 21, e.g. an inclination angle 2β in a range of 10° to 20°. In the embodiment of FIG. 3, the two cutting planes CP1, CP2 are each inclined in such a way that their respective intersecting lines with the x/z-reference plane V have an inclination angle β to the optical axis z of the lens nucleus 21, e.g. an inclination angle β in a range of 5° to 10°.

It should be pointed out that the embodiments illustrated in FIGS. 3 and 7 can be combined such that the two cutting planes CP1, CP2 are inclined to each other such that they define an inclination angle 2α in the x/y-reference plane R normal and an inclination angle 2β in the x/z-reference plane V.

As illustrated in FIGS. 6 and 7, in an embodiment the electronic circuit 10 or its computer program code, respectively, is configured to control the scanner system 12 to produce intracapsular tissue cuts by moving the focus F to intracapsular target locations on three cutting planes CP1, CP2, CP3 whereby the remaining third cutting plane CP3 runs through and/or parallel to the optical axis z of the lens nucleus 21. Accordingly, in this embodiment, the remaining third cutting plane CP3 divides each of the three lens nucleus slices (fragments F1, F2, F3) into half slices (lens nucleus fragments F11, F12, F21, F22, F31, F32).

It should be further pointed out that in further embodiments the third cutting plane CP3, which divides the three lens nucleus slices (fragments F1, F2, F3) into half slices (lens nucleus fragments F11, F12, F21, F22, F31, F32), can be positioned at a slight distance from the optical axis z of the lens nucleus 21, e.g. at a distance in a range of up to 0.5 mm or 1 mm at its closes point to the optical axis z, and/or the third cutting plane CP3 can be inclined to the optical axis z of the lens nucleus 21, e.g. with an inclination angle in a range of up to 10° or 20°.

In the embodiments illustrated in 2, 3, 5, 6, and 7, the electronic circuit 10 or its computer program code, respectively, is configured to control the scanner system 12 to produce intracapsular tissue cuts by moving the focus F to intracapsular target locations on three cutting planes CP1, CP2, CP3 whereby the two of the cutting planes CP1, CP2 are arranged such that the distance between the two of the cutting planes CP1, CP2 is greater than the phaco tip diameter with sleeve and smaller than half of an incision in the lens capsule 22 providing access to the lens nucleus 21, indicated schematically in FIGS. 2 and 3 as capsulotomy C. The diameter or length of the capsulotomy C is typically in the range of 5 mm to 6 mm, accordingly, the distance between the two of the cutting planes CP1, CP2 is in the range of 1.2 mm to 3 mm.

Figure 8:
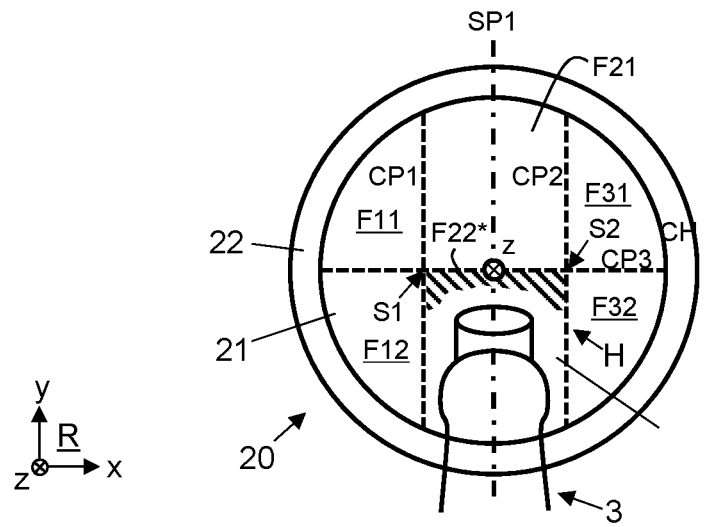
FIG. 8 shows a schematic top view of a lens of a human eye, after intracapsular fragmentation of the lens nucleus, with a phaco handpiece tip positioned in the anterior (top) part of half of an intermediary lens nucleus fragment, between two intracapsular tissue cuts which divide the lens nucleus into three fragments, in the process of emulsifying and removing this part, creating a void above a partial remainder of the intermediary lens nucleus fragment.
Figure 9:
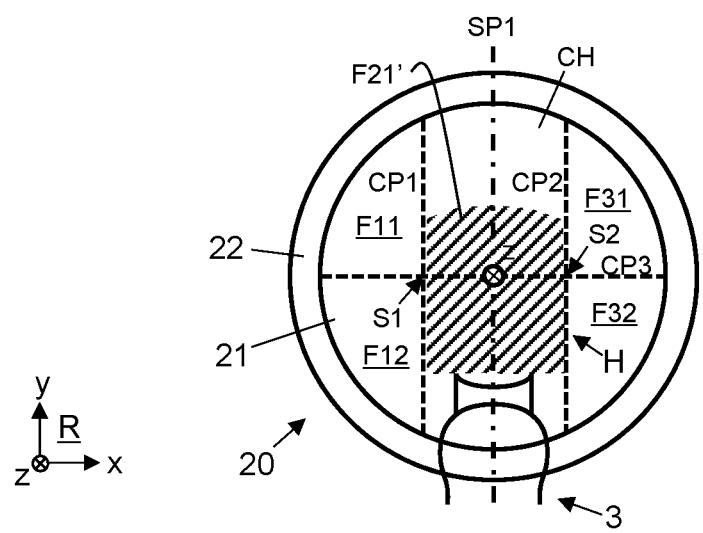
FIG. 9 shows a schematic top view of a lens of a human eye, after intracapsular fragmentation of the lens nucleus, with a phaco handpiece tip arranged inside the previously created void, in the process of emulsifying and removing the other half of the intermediary lens nucleus fragment.
Figure 10:
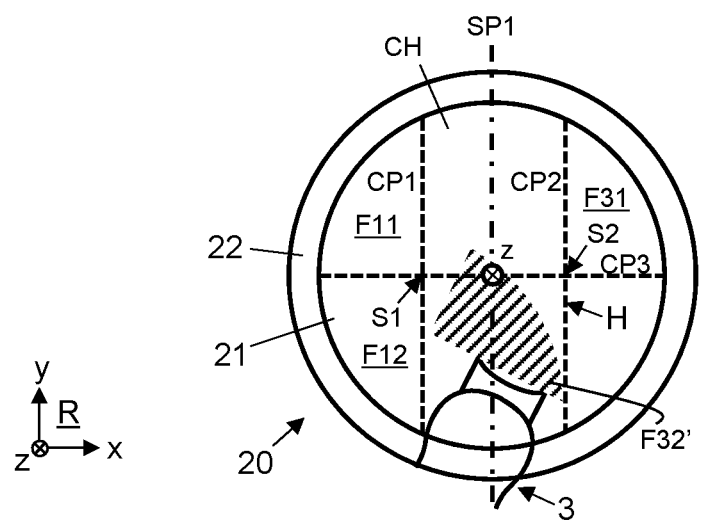
FIG. 10 shows a schematic top view of a lens of a human eye, after intracapsular fragmentation of the lens nucleus and after removal of intermediary lens nucleus fragments, ready for removal of the remaining lens nucleus fragments using suction of a phaco handpiece tip.

In the following paragraphs, described with reference to FIGS. 8-10 are intermediate states in the process of emulsifying and removing the lens nucleus 21 from the eye 2 using a phaco handpiece tip 3, subsequently to the intracapsular fragmentation of the lens nucleus 21, using the ophthalmological device 1 described above.

As illustrated schematically in FIG. 8, the intracapsular fragmentation of the lens nucleus 21 by the ophthalmological device 1 described above makes it possible to emulsify and remove an anterior top part, typically the top half of the lens fragment F22. The phaco handpiece tip 3 is inserted through an incision in the lens capsule 22, indicated schematically in FIGS. 2 and 3 as capsulotomy C, into said intermediary lens fragment F22. Ultrasonic energy is applied from the phaco handpiece tip 3 to said intermediary lens fragment F22 for progressively emulsifying and removing nucleus fragment tissue F22*, the upper part of fragment F22, using easy to learn "sculpting" movements only, up to the intracapsular tissue cuts along the intracapsular cutting planes CP1, CP2, CP3 defining the neighbouring lens nucleus fragments F12, F21, and F32, and leaving a posterior (bottom) part of the nucleus lens fragment F22 for later removal. Thereby an intracapsular (partial) channel or void CH is created, which provides access to and manoeuvring space for handling of the other fragments. The intracapsular (partial) channel or void CH makes it much easier to separate the remaining lens nucleus fragments F11, F12, F21, F31, F32 along the laser-prefragmented cutting planes, and to one by one sequentially emulsify and remove them by attaching the phaco handpiece tip 3 to the respective lens nucleus fragment, using some ultrasonic energy in combination with the suction generated by the pump 31 of the phaco emulsification system 300.

Specifically, once the intracapsular channel or void CH is created by removing the first half of the lens fragment F22, the phaco handpiece tip 3 is attached by suction to the anterior or upper half of lens fragment F21 and an additional spatula-like tool held by the other hand of the surgeon is inserted into the prefragmented cut plane CP1. Due to the laser-prefragmentation, and the presence of the initially created void, the nucleus fragments F1 and the remaining parts of nucleus fragment F2 can now be separated with only very little force along the cut plane CP1. Subsequently, the same procedure step is repeated to separate nucleus fragment F3 from the remaining parts nucleus fragment F2 along cut plane CP2. As illustrated in FIG. 9, once freed, the separated remaining parts of nucleus fragment F2 (bottom of lens fragment F22 and F21) can now easily be removed by attaching the phaco handpiece tip 3 to them and applying ultrasound energy and suction while using a tool controlled by the second hand of the surgeon to induce a rotating movement, feeding lens nucleus fragment material continuously into the phaco tip.

Once all of lens fragment F2 is removed from the lens capsule 22, leaving a "complete" intracapsular channel CH where the intermediary central slice F2 was previously located. One by one, the remaining lens nucleus fragments F11, F12, F31, F32 which are located adjacent to the intracapsular channel CH are first separated along the prefragmented cut plane CP3 and then removed from the lens capsule 22 by the phaco tip, as indicated in FIG. 10 for the separated tissue F32' of the lens nucleus fragment F32.

Advantageously, the inventive prefragmentation makes it possible to remove the nucleus fragments with a phaco tip while restricting application of ultrasonic energy to lens fragments moved to and positioned in a central area of the lens nucleus 21, away from the lens capsule 22, avoiding the risk of negatively impacting neighbouring tissue. Additionally, the inventive prefragmentation makes the subsequent manual manoeuvers for lens fragment removal easier to learn for inexperienced eye surgeons than those required after previous laser fragmentation patterns, thereby enhancing patient safety and increasing overall surgical efficacy.

The invention claimed is:

1. An ophthalmological device for intracapsular fragmentation of a lens nucleus of an eye, preparatory to emulsification and removal of the lens nucleus from the eye using a phaco handpiece tip, the ophthalmological device comprising:
 a laser source configured to generate a pulsed laser beam;
 a focusing optical module configured to make the pulsed laser beam converge onto a focus in the lens nucleus;
 a scanner system configured to move the focus to target locations in the lens nucleus; and
 an electronic circuit configured to control the scanner system to move the focus to intracapsular target locations on three cutting planes which extend from a posterior surface of the lens nucleus to an anterior surface of the lens nucleus for generating three intracapsular tissue cuts for the fragmentation of the lens nucleus into six nucleus fragments,
  wherein the three cutting planes form a maximum of two intracapsular intersecting lines on any of the cutting planes,
  a first cutting plane and a second cutting plane, of the three cutting planes, are arranged at a mutual distance larger than a diameter of the phaco handpiece tip, have an optical axis of the lens nucleus running therebetween without intracapsular intersection, and divide the lens nucleus into three nucleus fragments, and
  a third cutting plane, of the three cutting planes, forms intracapsular intersecting lines with the first cutting plane and the second cutting plane for subdividing each of the three nucleus fragments, thereby dividing the lens nucleus into the six nucleus fragments which are each larger than the diameter of the phaco handpiece tip and which are separated by the first cutting plane and the second cutting plane, not intersecting each other, and the third cutting plane, intersecting the first cutting plane and the second cutting plane.

2. The ophthalmological device of claim 1, wherein the electronic circuit is configured to control the scanner system to move the focus to intracapsular target locations on the first cutting plane and the second cutting plane whereby the first cutting plane and the second cutting plane are running essentially parallel to the optical axis of the lens nucleus.

3. The ophthalmological device of claim 1, wherein the electronic circuit is configured to control the scanner system to move the focus to intracapsular target locations on the first cutting plane and the second cutting plane whereby the first cutting plane and the second cutting plane are running essentially parallel to each other.

4. The ophthalmological device of claim 1, wherein the electronic circuit is configured to control the scanner system to move the focus to intracapsular target locations on the first cutting plane and the second cutting plane whereby the first cutting plane and the second cutting plane are inclined to each other and form an intersecting line outside the lens nucleus.

5. The ophthalmological device of claim 4, wherein the electronic circuit is configured to control the scanner system to move the focus to intracapsular target locations on the first cutting plane and the second cutting plane whereby the first cutting plane and the second cutting plane are inclined to each other, defining an inclination angle in a reference plane normal to the optical axis of the lens nucleus.

6. The ophthalmological device of claim 4, wherein the electronic circuit is configured to control the scanner system to move the focus to intracapsular target locations on the first cutting plane and the second cutting plane whereby the first cutting plane and the second cutting plane are inclined to each other, defining an inclination angle in a reference plane normal to a symmetry plane and running through the optical axis of the lens nucleus.

7. The ophthalmological device of claim 1, wherein the electronic circuit is configured to control the scanner system to move the focus to intracapsular target locations on the first cutting plane and the second cutting plane whereby the first cutting plane and the second cutting plane have a symmetry plane running through the optical axis of the lens nucleus.

8. The ophthalmological device of claim 1, wherein the electronic circuit is configured to control the scanner system to move the focus to intracapsular target locations on the third cutting plane whereby the third cutting plane runs through the optical axis of the lens nucleus.

9. The ophthalmological device of claim 1, wherein the electronic circuit is further configured to control the scanner system to move the focus to intracapsular target locations along adjacent scanning lines running in the three cutting planes for generating the intracapsular tissue cuts.

10. The ophthalmological device of claim 1, wherein the laser source comprises a femtolaser configured to generate a pulsed laser beam with femtosecond laser pulses.

11. The ophthalmological device of claim 1, wherein the focusing optical module comprises at least one movable lens configured to adjust a location of the focus along the optical axis of the lens nucleus.

12. The ophthalmological device of claim 1, wherein the scanner system comprises a divergence modulator configured to modulate a divergence of the pulsed laser beam for adjusting a location of the focus along the optical axis of the lens nucleus.

13. The ophthalmological device of claim 1, wherein the distance between the first cutting plane and the second cutting plane is greater than a third of a diameter of the lens nucleus.

14. The ophthalmological device of claim 1, wherein the electronic circuit is configured to control the scanner system to move the focus to intracapsular target locations on the first cutting plane, the second cutting plane, and the third cutting plane, whereby the first cutting plane, the second cutting plane, and the third cutting plane form an essentially H-shaped intersection with a reference plane normal to the optical axis of the lens nucleus.

15. A computer program product comprising a non-transitory computer-readable medium having stored thereon computer program code for controlling a processor of an ophthalmological device which comprises a laser source configured to generate a pulsed laser beam, a focusing optical module configured to make the pulsed laser beam converge onto a focus in a lens nucleus of an eye, and a scanner system configured to move the focus to target locations in the lens nucleus, whereby the computer program product is configured to control the processor such that the processor directs the scanner system to move the focus to intracapsular target locations on three cutting planes which extend from a posterior surface of the lens nucleus to an anterior surface of the lens nucleus for generating three intracapsular tissue cuts for the fragmentation of the lens nucleus into six nucleus fragments, wherein the three cutting planes form a maximum of two intracapsular intersecting lines on any of the cutting planes, a first cutting plane and a second cutting plane, of the three cutting planes, are arranged at a mutual distance larger than a diameter of the phaco handpiece tip, have an optical axis of the lens nucleus running therebetween without intracapsular intersection, and divide the lens nucleus into three nucleus fragments, and a third cutting plane, of the three cutting planes, forms intracapsular intersecting lines with the first cutting plane and the second cutting plane for subdividing each of the three nucleus fragments, thereby dividing the lens nucleus into the six nucleus fragments which are each larger than the diameter of the phaco handpiece tip and which are separated by the first cutting plane and the second cutting plane, not intersecting each other, and the third cutting plane, intersecting the first cutting plane and the second cutting plane.

16. A device comprising:
a scanner system configured to move a focus in a lens nucleus; and
an electronic circuit configured to control the scanner system to move the focus to intracapsular target locations on a plurality of cutting planes which extend from a posterior surface of the lens nucleus to an anterior surface of the lens nucleus for generating three intracapsular tissue cuts for the fragmentation of the lens nucleus into six nucleus fragments,
wherein the plurality of cutting planes form a maximum of two intracapsular intersecting lines on any of the plurality of cutting planes,
wherein a first cutting plane and a second cutting plane, of the plurality of cutting planes, are arranged at a mutual distance larger than a diameter of a phaco handpiece tip, have an optical axis of the lens nucleus running there between without intracapsular intersection, and divide the lens nucleus into three nucleus fragments,
wherein a third cutting plane, of the plurality of cutting planes, forms intracapsular intersecting lines with the first cutting plane and the second cutting plane for subdividing each of the three nucleus fragments, thereby dividing the lens nucleus into the six nucleus fragments which are each larger than the diameter of the phaco handpiece tip and which are separated by the first cutting plane and the second cutting plane, not intersecting each other, and the third cutting plane, intersecting the first cutting plane and the second cutting plane.

17. The device of claim 16, further comprising a laser source configured to generate a pulsed laser beam.

18. The device of claim 17, further comprising a focusing optical module configured to make the pulsed laser beam converge onto the focus in the lens nucleus.

19. The device of claim 16, further comprising a focusing optical module configured to make a pulsed laser beam converge onto the focus in the lens nucleus.

20. The device of claim 16, wherein the electronic circuit is further configured to control the scanner system to move the focus to intracapsular target locations on the first cutting plane and the second cutting plane whereby the first cutting plane and the second cutting plane have a symmetry plane running through the optical axis of the lens nucleus.

21. A method comprising:
generating, by a laser source, a pulsed laser beam;
making, by a focusing optical module, the pulsed laser beam converge onto a focus in a lens nucleus of an eye;
moving, by a scanner system, the focus to target locations in the lens nucleus; and
controlling, by an electronic circuit, the scanner system to move the focus to intracapsular target locations on three cutting planes which extend from a posterior surface of lens nucleus to an anterior surface of the lens nucleus for generating three intracapsular tissue cuts for fragmentation of the lens nucleus into six nucleus fragments,
wherein:
the three cutting planes form a maximum of two intracapsular intersecting lines on any of the cutting planes,
a first cutting plane and a second cutting plane, of the three cutting planes, are arranged at a mutual distance larger than a diameter of a phaco handpiece tip, have an optical axis of the lens nucleus running therebetween without intracapsular intersection, and divide the lens nucleus into three nucleus fragments, and
a third cutting plane, of the three cutting planes, forms intracapsular intersecting lines with the first cutting plane and the second cutting plane for subdividing each of the three nucleus fragments, thereby dividing the lens nucleus into the six nucleus fragments which are each larger than the diameter of the phaco handpiece tip and which are separated by the first cutting plane and the second cutting plane, not intersecting each other, and the third cutting plane, intersecting the first cutting plane and the second cutting plane.

* * * * *